(12) United States Patent
Strähle et al.

(10) Patent No.: US 8,035,821 B2
(45) Date of Patent: Oct. 11, 2011

(54) INTERFEROMETRIC SYSTEM HAVING A REFERENCE SURFACE INCLUDING A MIRRORED ZONE

(75) Inventors: Jochen Strähle, Weissach (DE); Ulrich Kallmann, Tuebingen (DE); Rahmi Gencoglu, Nilüfer/Bursa (TR); Uwe Kasten, Moeglingen (DE)

(73) Assignee: Robert Bosch GmbH, Stuttgart (DE)

( * ) Notice: Subject to any disclaimer, the term of this patent is extended or adjusted under 35 U.S.C. 154(b) by 622 days.

(21) Appl. No.: 11/663,614

(22) PCT Filed: Jul. 18, 2005

(86) PCT No.: PCT/EP2005/053445
§ 371 (c)(1),
(2), (4) Date: Mar. 21, 2007

(87) PCT Pub. No.: WO2006/032553
PCT Pub. Date: Mar. 30, 2006

(65) Prior Publication Data
US 2009/0201511 A1   Aug. 13, 2009

(30) Foreign Application Priority Data
Sep. 22, 2004   (DE) .......................... 10 2004 045 802

(51) Int. Cl.
*G01B 11/02* (2006.01)
(52) U.S. Cl. ...................................................... 356/511
(58) Field of Classification Search ............... 356/489, 356/497, 511–513
See application file for complete search history.

(56) References Cited

U.S. PATENT DOCUMENTS

| | | | |
|---|---|---|---|
| 3,788,746 A * | 1/1974 | Baldwin et al. | 356/485 |
| 6,268,921 B1 | 7/2001 | Seitz et al. | |
| 6,721,094 B1 | 4/2004 | Sinclair et al. | |
| 7,483,149 B2 * | 1/2009 | Strahle | 356/512 |

FOREIGN PATENT DOCUMENTS

| | | |
|---|---|---|
| DE | 41 08 944 | 9/1992 |
| DE | 197 21 843 | 2/1999 |
| DE | 197 38 900 | 3/1999 |
| DE | 198 08 273 | 9/1999 |
| GB | 673971 | 6/1952 |
| JP | 49-70649 | 7/1974 |
| JP | 63 259404 | 10/1988 |

OTHER PUBLICATIONS

Patents Abstracts of Japan, vol. 013, No. 073, Feb. 20, 1989.

* cited by examiner

*Primary Examiner* — Michael A Lyons
(74) *Attorney, Agent, or Firm* — Kenyon & Kenyon LLP

(57) ABSTRACT

An interferometric system having an illumination arm, including a light source and an illuminating optical system, for forming an illuminating beam; an object arm, including a reference element for measuring an object having an object surface to be measured, for forming an image-rays path, the object to be measured having an object surface inaccessible to direct illumination; a reference arm including a reference element; a detector arm including a detector; and a beam splitter, the reference element having one or more mirrored zones. Consequently, component parts which have undercut surfaces in the illumination direction can be measured in a single measuring operation.

16 Claims, 3 Drawing Sheets

INTERFEROMETRIC SYSTEM HAVING A REFERENCE SURFACE INCLUDING A MIRRORED ZONE

FIELD OF THE INVENTION

The present invention relates to an interferometric system having an illumination arm, including a light source and an illuminating optical system, for forming an illuminating beam; having an object arm, including a reference element for measuring an object having an object surface to be measured, for forming an image-rays path, the object to be measured having an object surface inaccessible to direct illumination; having a reference arm including a reference element; having a detector arm including a detector; and having a beam splitter.

The present invention further relates to a measuring method able to be carried out using the device.

BACKGROUND INFORMATION

The manufacturing of precision parts requires measuring methods for recording the geometry and the state of the parts in order to ensure the quality of the corresponding parts. Optical measuring methods such as image acquisition and image evaluation, interferometry, particularly white-light interferometry, makes an important contribution here.

The principle of the white-light interferometer is based on the fact that a short-coherent light source is used for the illumination of an imaging system. In addition to the normal imaging optics, the imaging system has a reference arm which is traversed by a portion of the irradiated light. If the transit path of the light $\Lambda_o$ in the object arm and the transit path in the reference arm $\Lambda_R$ now have a path difference that is less than the coherence length $I_c$ of the light, i.e.

$$|\Lambda_R - \Lambda_O| < I_C \quad (1)$$

then the light fields brought together again can exhibit a measurable interference. This is utilized in that, during the measurement, the path difference of the light fields, defined by the shift of the object or the reference element along the optical axis, is altered. At the same time, the intensity of the reunited light fields is measured on a detector, usually a CCD camera, measuring in planar fashion. Since a constructive or destructive interference can only take place within the coherence length of the white-light source, the pixel-by-pixel evaluation of the intensity modulation produced by the interference, the intensity correlogram, supplies clear information concerning height for each individual pixel. Carried out for the entire pixel field, this results in complete height information for the object.

Commercial white-light interferometers typically have the following specifications:

The height resolution $\Delta z$ is given by the average utilized wavelength of the light $\lambda_m$, the coherence length $I_c$ and the type of correlogram evaluation algorithm. Typical parameters such as $\lambda_m = 600$ nm, $I_c = 2$ μm permit values of $\Delta z = 1$ nm.

The lateral resolution $\delta$ is equal to that of a conventional imaging system and, in principle, is limited by $\lambda_m$ and the numerical aperture NA of the imaging optics.

$$\delta \geq 0.61 \lambda_m / NA \quad (2)$$

The maximum measurable total height difference $z_{max}$ is determined by the technical feasibility of producing a path difference in the reference arm and object arm that is guided precisely over the entire distance. Regulated piezosystems today permit values of $z_{max} \geq 400$ μm.

Conventional interferometers, particularly white-light interferometer systems, can be used for the tasks described above when the location to be measured is easily accessible and has a predominantly flat geometry. If this is not the case, interferometers are used which have special optics adapted to the object to be measured. However, these interferometers have the disadvantage that undercuts on the object to be measured lie in the shadow area of the illumination and therefore cannot be recorded. To measure these surfaces, the object must be dismounted and measured in a second measuring operation.

SUMMARY

An object of the present invention is to provide an interferometric system that allows a 3-dimensional measurement of objects having hard-to-access surfaces, using a single mount.

This object of the present invention relating to the device may be achieved in that the reference element has one or more mirrored zones. The light beams thereby reach undercut surfaces, permitting them to be measured in the same measuring operation as the remaining surfaces. In particular, it is possible to determine the position of the undercut surfaces relative to the remaining surfaces.

Undercuts of any form, even those having surfaces which are not even, can be measured by adapting the mirrored zone to the object, to the effect that in each case, the mirrored zone is formed in the half angle to the perpendicular with respect to the optical axis of the image-rays path, like a partial surface to be measured on the object surface.

One specific example embodiment that is especially insensitive to environmental influences such as the influence of temperature provides that the mirrored zone is joined in one piece with the reference element.

If the mirrored zone is implemented as a separate unit and if it is joined mechanically to the reference element, e.g., by adhesive bonding or screwing, in a separate processing step, it may be adapted to the shape of the object surface and, if applicable, be reused in another reference element when working with a substantially identical object.

In one preferred specific embodiment, in addition to the mirrored zone, a second reference surface for measuring the object surface is formed in the reference element. It is thereby possible to determine the relative position of an object surface accessible for the customary measuring method and the surface that is usually not accessible.

If, in addition to the mirrored zone, at least one second reference surface for measuring at least one second object surface is formed in the reference element, in a depth scan, it is possible to determine the position of all object surfaces of interest in relation to the reference element.

The object of the present invention relating to the method may be achieved in that light beams reflected by an object surface are brought to interference with light beams reflected by an associated reference surface, while light beams reflected by the object surface inaccessible to direct illumination are additionally reflected via a mirrored zone and then brought to interference with light beams reflected by an associated reference surface. In this way, component parts having undercuts may be measured in a single measuring operation, and, in particular, it is possible to determine the relative position of the undercuts with respect to the remaining surfaces.

BRIEF DESCRIPTION OF THE DRAWINGS

The present invention is explained in greater detail below with reference to exemplary embodiments shown in the figures.

DESCRIPTION OF EXAMPLE EMBODIMENTS

Figure 1:
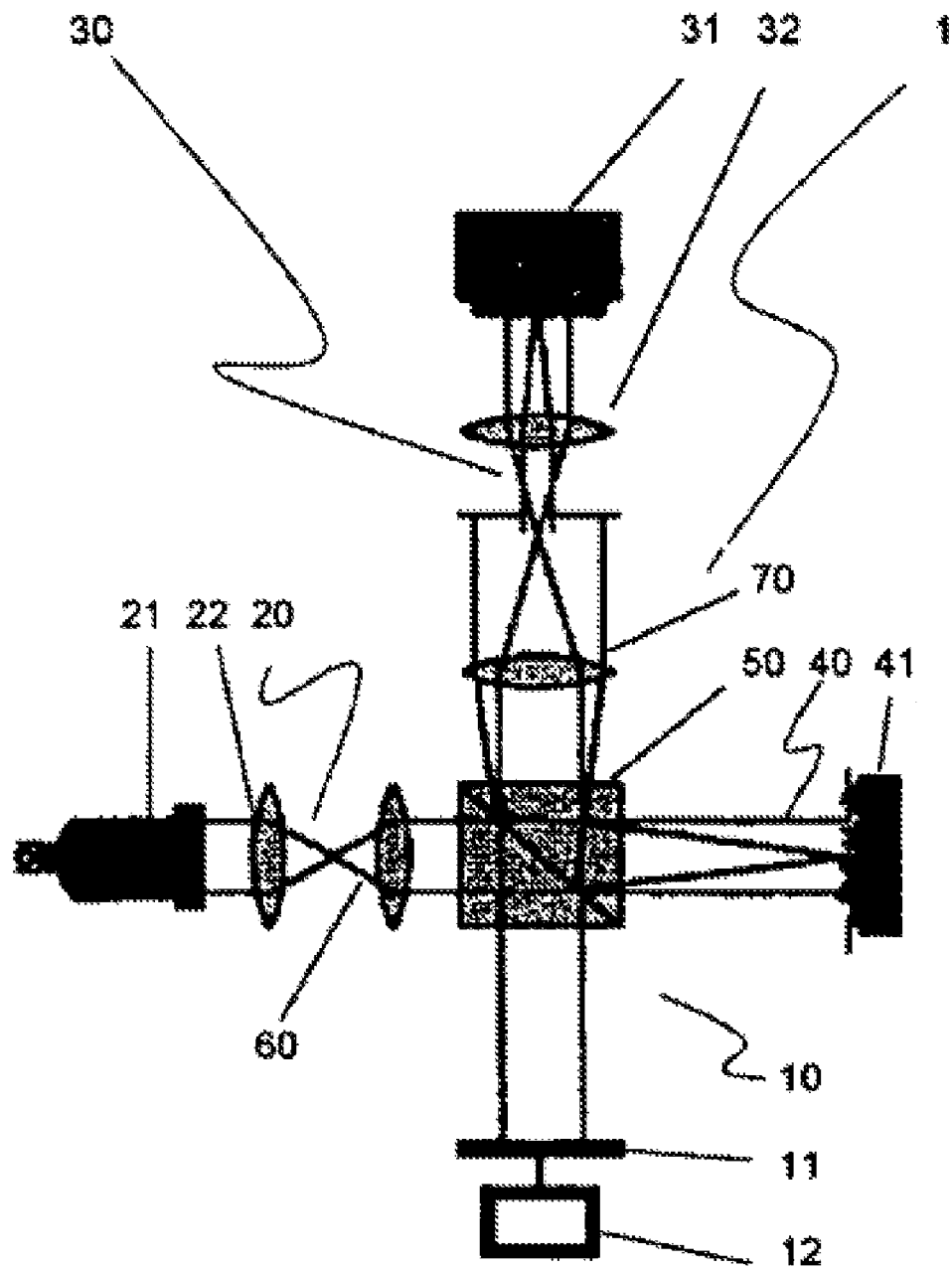
FIG. 1 shows schematically a conventional white-light interferometer configuration.

Interferometric system 1 of a white-light interferometer configuration according to the related art shown schematically in FIG. 1 includes an object arm 40, in which the surface to be measured on an object 41 is located, and an illumination arm 20 which has a light source 21 and an illuminating optical system 22, composed of one or more lenses, which form an illuminating beam path 60. Situated orthogonally with respect to illumination arm 20 and object arm 40, interferometric system 1 has a reference arm 10 having a reference element 11 that is coupled mechanically to an adjusting element 12, usually a piezosystem. Diametrically opposite reference arm 10 is a detector arm 30 which has a detector 31, usually a detector 31 measuring in planar fashion such as a CCD camera, as well as a lens 32 for imaging an intensity distribution to be evaluated in image-rays path 70. An evaluation unit (not shown) is provided for the evaluation.

In this context, a beam splitter 50 splits up the various light beams and brings them together again, so that the light beams from reference arm 10 and those from object arm 40 are able to interfere in detector arm 30 at detector 31 in the manner described above.

The object may be scanned by shifting reference element 11 using adjusting element 12 or, alternatively, by shifting object 41 using a similar adjusting element.

The architecture of a conventional interferometric system 1 allows only the measurement of surfaces on object 41 which are directly accessible to the illumination. Undercuts in object 41 require that the object be dismounted, and that these surfaces as well as further object surfaces be measured in a second operation, in order to determine the position of the undercuts with respect to the object surfaces measured in the first cut.

Figure 2:
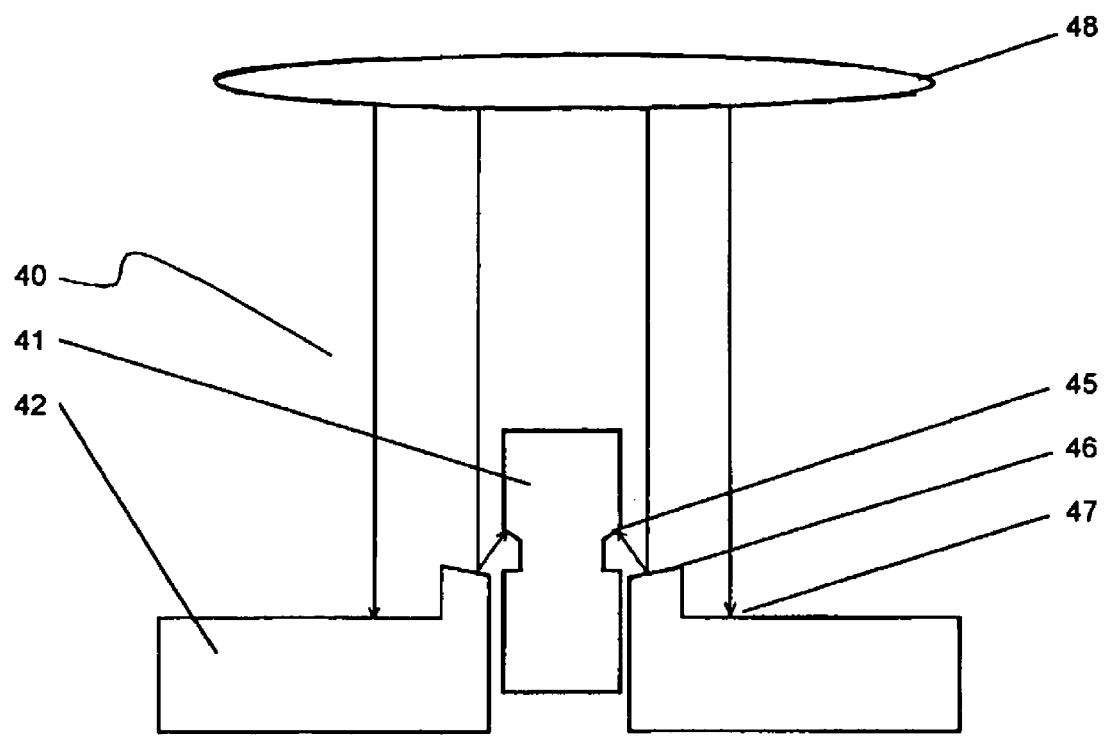
FIG. 2 shows schematically an example interferometric system.

In contrast, FIG. 2 shows schematically an interferometric system 1 in which, according to the present invention, object surfaces 45 on object 41 which are inaccessible to direct illumination are measured. To that end, object 41 is connected to a reference element 42 that has at least one mirrored zone 46.

The light emerges from illumination arm 20 (not shown here) through a lens 48 in the direction of object 41. The portion striking mirrored zone 46 is reflected in the direction of object surface 45 inaccessible to direct illumination. Reflected back from there and via mirrored zone 46, it passes through lens 48 and is supplied via beam splitter 50 (not shown here) to detector 31 (likewise not shown). Used as reference for object surface 45 is a reference surface 47 whose reflected light traverses the same optical path length as that reflected by object surface 45, and therefore produces the same interference pattern.

Figure 3:
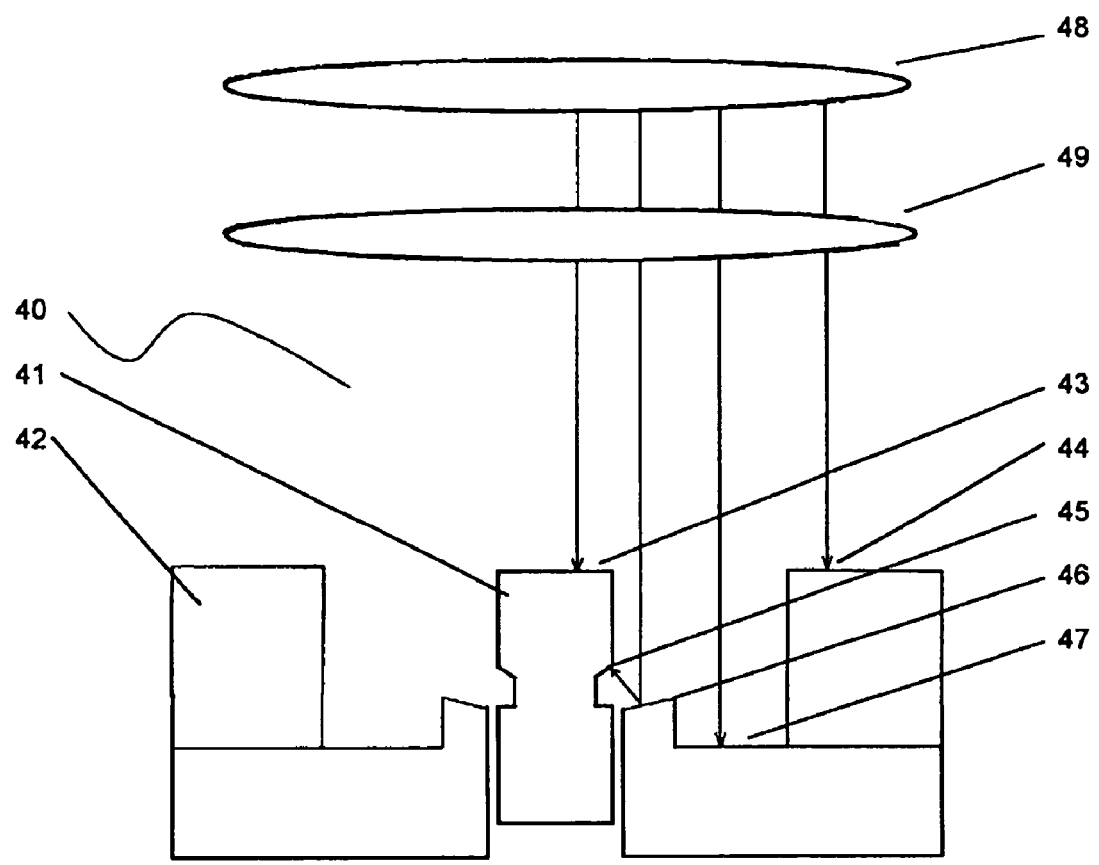
FIG. 3 shows schematically an interferometric system which is suitable for the simultaneous measurement of surfaces facing toward and away from the objective.

FIG. 3 shows a specific embodiment for interferometric system 1 which permits a measurement of a complete object 41 having undercuts. To that end, in object arm 40, lens 48 is brought into at least one second position, represented here by lens 49. This brings about a depth scan over object 41. While in the position of lens 48, object surface 43 and associated reference surface 44 contribute to interference, in the position of lens 49, object surface 45 and associated reference surface 47 are measured, object surface 45 being measured with the aid of mirrored zone 46. In this way, all surfaces of interest on object 41 may be measured relative to one another. Thus, given a suitable embodiment of reference element 42 having mirrored zones 46, it is possible to reach all object surfaces of interest.

What is claimed is:

1. An interferometric system, comprising:
an illumination arm having a light source and an illuminating optical system to form an illuminating beam path;
an object arm, having a reference element to measure an object, to form an image-ray path, the object to be measured having an object surface inaccessible to direct illumination;
a reference arm;
a detector arm having a detector; and
a beam splitter;
wherein the reference element has a first reference surface and at least one mirrored zone for measuring the object surface inaccessible to direct illumination,
wherein the reference element has a second reference surface for measuring an object surface accessible to direct illumination, and wherein light beams are reflected by the object surface accessible to direct illumination as well as by the object surface inaccessible to direct illumination.

2. The device as recited in claim 1, wherein the at least one mirrored zone is adapted to the object to the effect that the at least one mirrored zone is in each case formed in a half angle to a perpendicular with respect to an optical axis of the image-ray path.

3. The device as recited in claim 1, wherein the at least one mirrored zone is joined in one piece with the reference element.

4. The device as recited in claim 1, wherein the at least one mirrored zone is implemented as a separate unit and is joined mechanically to the reference element.

5. The device as recited in claim 4, wherein the at least one mirrored zone is joined mechanically to the reference element by one of adhesive bonding or screwing.

6. The device as recited in claim 1,
wherein the second reference surface is formed in the reference element.

7. The device as recited in claim 1, further comprising:
at least one further reference surface to measure at least one further object surface, the at least one further reference surface being formed in the reference element.

8. A method for operating an interferometric system, the interferometric system including an illumination arm, having a light source and an illuminating optical system to form an illuminating beam path, an object arm having a reference element to measure an object to form an image-ray path, the object to be measured having an object surface inaccessible to direct illumination, a reference arm, a detector arm having a detector, and a beam, the method comprising:
bringing light beams reflected by an object surface accessible to direct illumination to interference with light beams reflected by a reference surface, while light beams reflected by the object surface inaccessible to direct illumination are reflected via a mirrored zone and then brought to interference with light beams reflected by an associated reference surface.

9. An interferometric system for measuring an object, comprising:
- an illumination arm having a light source and an illuminating optical system to form an illuminating beam path;
- an object arm, having a reference element, to form an image-ray path, the object to be measured having an object surface inaccessible to direct illumination;
- a reference arm;
- a detector arm having a detector; and
- a beam splitter;
- wherein the reference element in the object arm has a reference surface and at least one mirrored zone for reflecting light beams from the illuminating beam path in the direction of the object surface inaccessible to direct illumination, the light beams reflected via the at least one mirrored zone interfering with light beams reflected on the reference surface.

10. The device as recited in claim 9, wherein the at least one mirrored zone is adapted to the object to the effect that the at least one mirrored zone is in each case formed in a half angle to a perpendicular with respect to an optical axis of the image-ray path.

11. The device as recited in claim 9, wherein the at least one mirrored zone is joined in one piece with the reference element.

12. The device as recited in claim 9, wherein the at least one mirrored zone is implemented as a separate unit and is joined mechanically to the reference element.

13. The device as recited in claim 9, wherein the at least one mirrored zone is joined mechanically to the reference element by one of adhesive bonding or screwing.

14. The device as recited claim 9, further comprising:
a second reference surface to measure the object surface, the second reference surface being formed in the reference element.

15. The device as recited in claim 9, further comprising:
at least one second reference surface to measure at least one second object surface, the at least one second reference surface being formed in the reference element.

16. A method for operating an interferometric system for measuring an object, the interferometric system including an illumination arm having a light source and an illuminating optical system to form an illuminating beam path, an object arm, having a reference element, to form an image-ray path, the object to be measured having an object surface inaccessible to direct illumination, a reference arm, a detector arm having a detector, and a beam splitter, the method comprising:
bringing light beams reflected by an object surface inaccessible to direct illumination that are additionally reflected via at least one mirrored zone to interference with light beams reflected by an associated first reference surface, while light beams reflected by a second object surface are brought to interference with light beams reflected by an associated second reference surface, the associated first reference surface, the associated second reference surface, and the at least one mirrored zone being provided in the reference element situated in the object arm.

* * * * *